US010660859B2

(12) United States Patent
Vertommen et al.

(10) Patent No.: US 10,660,859 B2
(45) Date of Patent: May 26, 2020

(54) ENTERIC COATING FOR SOFT CAPSULE

(71) Applicant: Capsugel Belgium NV, Bornem (BE)

(72) Inventors: Jan Vertommen, Grimbergen (BE); Marie Sophie Martina, Strasbourg (FR)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 14/655,049

(22) PCT Filed: Mar. 3, 2014

(86) PCT No.: PCT/IB2014/059407
§ 371 (c)(1),
(2) Date: Jun. 23, 2015

(87) PCT Pub. No.: WO2014/140991
PCT Pub. Date: Sep. 18, 2014

(65) Prior Publication Data
US 2015/0342892 A1 Dec. 3, 2015

Related U.S. Application Data

(60) Provisional application No. 61/792,584, filed on Mar. 15, 2013.

(51) Int. Cl.
| | |
|---|---|
| *A61K 9/48* | (2006.01) |
| *A61K 47/14* | (2017.01) |
| *A61K 47/32* | (2006.01) |
| *A61K 47/26* | (2006.01) |
| *C09D 133/02* | (2006.01) |
| *C09D 133/08* | (2006.01) |
| *C08K 5/11* | (2006.01) |
| *C08K 5/103* | (2006.01) |
| *C08K 5/1535* | (2006.01) |
| *A23K 10/00* | (2016.01) |
| *A23P 10/30* | (2016.01) |
| *A23L 33/10* | (2016.01) |
| *A61K 9/50* | (2006.01) |
| *A61K 9/28* | (2006.01) |

(52) U.S. Cl.
CPC ............ *A61K 9/4891* (2013.01); *A23K 10/00* (2016.05); *A23L 33/10* (2016.08); *A23P 10/30* (2016.08); *A61K 9/4808* (2013.01); *A61K 47/14* (2013.01); *A61K 47/26* (2013.01); *A61K 47/32* (2013.01); *C08K 5/103* (2013.01); *C08K 5/11* (2013.01); *C08K 5/1535* (2013.01); *C09D 133/02* (2013.01); *C09D 133/08* (2013.01); *A23V 2002/00* (2013.01); *A61K 9/2846* (2013.01); *A61K 9/5026* (2013.01)

(58) Field of Classification Search
None
See application file for complete search history.

(56) References Cited

U.S. PATENT DOCUMENTS

| | | | |
|---|---|---|---|
| 5,851,579 A | 12/1998 | Wu et al. | |
| 2005/0095285 A1* | 5/2005 | Rao | A61K 9/4816 424/456 |
| 2011/0002986 A1* | 1/2011 | Durig | A61K 9/4891 424/463 |

FOREIGN PATENT DOCUMENTS

| | | |
|---|---|---|
| EP | 2283830 | 2/2011 |
| EP | 2465496 | 6/2012 |
| EP | 2911654 | 9/2015 |
| WO | WO2013/035081 | 3/2013 |

OTHER PUBLICATIONS

Cole et al., "Enteric coated HPMC capsules designated to achieve intestinal targeting," *International Journal of Pharmaceutics*, 231(1), pp. 83-95 (Jan. 2002).
European Patent Application No. 14710393.1 filed Mar. 3, 2014.
International Search Report and Written Opinion for PCT/IB2014/059407 (dated Apr. 23, 2014).
International Preliminary Report on Patentability for PCT/IB2014/059407 (dated Sep. 24, 2015).
Hutchison, K. G. et al., "Soft gelatin capsules," in *Aulton's Pharmaceutics: The Design & Manufacture of Medicines*, Ch. 13, pp. 527-538 (Michael E. Aulton, Ed., 3rd Ed., 2007).
Pereit et al., "Glyceryl Monostearate as a Glidant in Aqueous Film-Coating Formulations," *Eur. J Pharm. Biopharm.*, 41(4):219-228 (Aug. 1995) (Abstract Only).
Office Action from the European Patent Office for European Patent Application No. 14710393.1, dated Dec. 1, 2016.
Wesseling et al., "Tackiness of acrylic and cellulosic polymer films used in the coating of solid dosage forms," *Eur. J Pharm. Biopharm.*, 47(1):73-78 (Jan. 1999).
Office Action from the European Patent Office for European Patent Application No. 14710393.1, dated Aug. 8, 2018.

* cited by examiner

*Primary Examiner* — Tigabu Kassa
(74) *Attorney, Agent, or Firm* — Klarquist Sparkman, LLP

(57) ABSTRACT

The present disclosure relates to a novel aqueous coating composition comprising a polymer, at least one glidant, and at least one emulsifier, and at least one plasticizer, for soft capsule shells or softgel capsules, providing an enteric release profile, and to a method of enteric coating of soft capsule shells or containers; and to the resulting enteric coated soft capsule shells or softgel capsules with the aqueous coating composition.

12 Claims, 2 Drawing Sheets

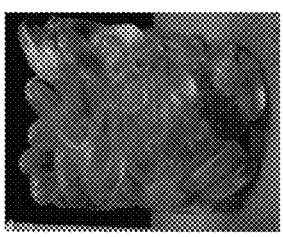
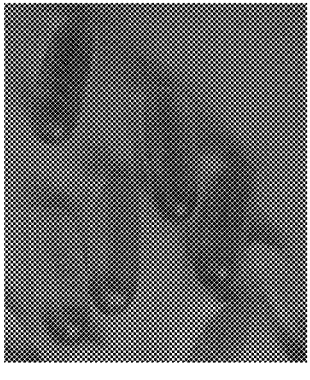
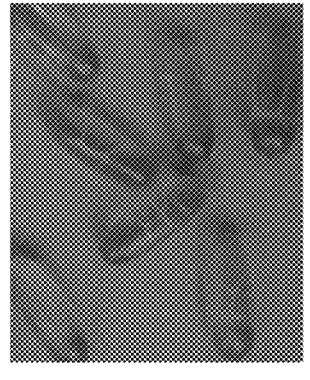

ENTERIC COATING FOR SOFT CAPSULE

CROSS REFERENCE TO RELATED APPLICATIONS

This is the U.S. National Stage of International Application No. PCT/IB2014/059407, filed Mar. 3, 2014, which was published in English under PCT Article 21(2), which in turn claims the benefit of U.S. Provisional Application No. 61/792,584, filed Mar. 15, 2013. The provisional application is incorporated herein in its entirety.

The present disclosure relates to a novel aqueous coating composition for soft capsule containers or shells, providing an enteric release profile, and to a method of enteric coating of soft capsule shells or softgel containers; and to the resulting enteric coated soft capsule shells or softgel containers. The enteric coated soft capsule shells according to the disclosure have reduced cracking and sticking and have high flexibility. The present disclosure relates to the use of such enterically coated softgel containers particularly but not exclusively for oral administration of at least one of pharmaceuticals, veterinary products, foods and dietary supplements to humans or animals.

Capsules are widely used in the pharmaceutical field as oral dosage form containers for administration to humans and animals of, e.g., pharmaceuticals, veterinary products, foods, and dietary supplements. Advantages of capsules over other dosage forms may include better patient compliance, greater flexibility in dosage form design, and less expensive manufacturing processes. Pharmaceutical capsules are conventionally divided into soft shell capsules (hereinafter softgel capsules) and hard shell capsules (hereinafter hard capsules). The characteristics of softgel and hard capsules are well known in the pharmaceutical field.

Hard capsule shells are generally manufactured using dip molding processes involving the use of pins dipped into solutions of the different ingredients that are needed for the making of the capsule shell containers. Methods for the manufacturing of soft gelatin or softgel capsule shells are also known in the art and are different from hard capsule shell manufacturing. Manufacturing of soft gelatin or softgel capsule shells at a production scale was introduced by Robert Pauli Scherer in 1933 with the invention of a rotary die encapsulation machine. The rotary die process involves continuous formation of a heat seal between two ribbons of gelatin simultaneous with dosing of the fill liquid into each capsule. Although manufacturing process speed and efficiency has improved with time, the basic manufacturing principle remains essentially unchanged. Before the encapsulation process takes place, two sub-processes are often carried out simultaneously, yielding the two components of a softgel capsule: (a) the gel mass which will provide the softgel capsule shell, and (b) the fill matrix for the softgel capsule contents. Softgel capsules have a continuous gelatin shell surrounding a liquid core, and are formed, filled, and sealed in one operation.

Softgel capsule walls are typically thicker than two-piece hard gelatin capsules, and their walls comprise plasticizers such as, for example, glycerol, sorbitol and/or propylene glycol to make the shell elastic. Processes for making softgel capsule shells are known, and softgel capsules are available commercially. See, e.g., Aulton, M., *Aulton's Pharmaceutics: The Design & Manufacture of Medicines,* 527-533 (Kevin M G Taylor, Ed., 3rd Ed., 2001). Softgel capsules have various advantages; they may show improved drug absorption, be easier to swallow, avoid dust handling issues, and have increased stability compared to other dosage forms. Softgel capsules may be filled with liquid fill such as oils and/or lipid soluble active ingredients such as pharmaceuticals, veterinary products, foods and dietary supplements.

In certain containers for oral administration, enteric release is desirable and may be provided by an enteric coating. Such an enteric coating prevents the active ingredients in the capsule from being released in the stomach, and allows the active ingredient(s) or beneficial substance(s) to be released once the dosage form has passed into the small intestinal tract. Thus, polymeric materials that are suitable for enteric coating applications should be insoluble in a low pH medium typically having a value less than about pH 3.5, but soluble in a higher pH medium typically having a value greater than about pH 5.5. Thus, the objectives for using enteric coating materials in pharmaceutical dosage forms include: a) to protect the stomach from the harmful effect(s) of an active ingredient; b) to protect the active ingredient from the adverse effect(s) of gastric fluid; c) to deliver an active ingredient to a particular region of the intestine; and/or d) to provide a sustained release dosage form to the gastrointestinal tract.

Different techniques have been used to impart enteric release properties to the hard or softgel capsule shells. One such technique involves treating the surface of the pre-manufactured capsules (e.g., spraying or film-coating already manufactured capsules) with one or more layers of a substance or composition that is known to impart enteric properties. For soft capsules, the post-treatment spraying or film coating may result in shells that are brittle and hard to handle, or that agglomerate into a non-functional mass.

Various enteric polymer coatings are known in the pharmaceutical field. While organic solvent based coating is known, aqueous based polymer coating is more commonly utilized in modern pharmaceutical dosage forms due to decreased environmental issues and advantages of the mechanics of spray rates.

Examples of enteric polymers for use on container coatings include shellac, cellulose acetate trimellitate (CAT), various hydroxypropyl cellulose polymers (i.e., HPMC, HPMCP, HPMCAS), and phthalates such as cellulose acetate phthalate (CAP) and polyvinyl acetate phthalate (PVAP). Each of these polymers has disadvantages. Shellac, a natural product derived from an insect secretion, may be subject to inconsistent supply and unacceptable variations in quality. Cellulose acetate trimellitate requires the impractical and potentially undesirable addition of ammonium hydroxide (Wu et al., U.S. Pat. No. 5,851,579). Hydroxypropylcellulose polymers may be unstable upon longer term storage, particularly under conditions of high humidity.

Examples of polymers used to achieve enteric properties in container coatings include anionic polymethacrylates (copolymers of methacrylic acid and either methyl methacrylate or ethyl acrylate) (EUDRAGIT®) such as EUDRAGIT® L 30 D-55 (Methacrylic Acid Copolymer Dispersion, NF), which is soluble at a pH above about 5.5.

However, enteric coatings for softgel capsules must provide practical solutions for this type of dosage form. Such coatings must be stable, must not impart undesirable stickiness, and must not adversely affect characteristics of dissolution and/or brittleness in the finished softgel dosage form.

SUMMARY

The instant disclosure relates to an innovative enteric coating formulation for softgel capsules having selective concentrations of glidant, emulsifier, and plasticizer.

A lower percentage of glidant in the coating composition, as typically reported in the art (Pereit et al., 1995, *Eur. J Pharm. Biopharm.* 41, 219-228; Wesseling et al., 1999, *Eur. J Pharm. Biopharm.* 47, 73-78), failed to prevent severe stickiness of the coated capsules during storage. Reduction of the emulsifier as typically reported literature concentrations (Cole et al., 2002, *Int. J. Pharm.* 231, 83-95, Wesseling et al., 1999, *Eur. J Pharm. Biopharm.* 47, 73-78) resulted in cracking of the coating.

Surprisingly, the enteric coating according to the present disclosure confers high flexibility to softgel capsules, even for unfavorable geometries such as size 20 Oblong capsules, while also preventing tackiness over time.

BRIEF DESCRIPTION OF THE DRAWINGS

FIGS. 1A-1D show the physical-mechanical properties of enterically coated size 20 oblong softgel capsules according to the additive content in coating formation, expressed as dry copolymer content. FIG. 1A shows softgel capsules coated with a formulation of 5% polysorbate 80 and 5% glycerol monostearate shortly after coating (T0). FIG. 1B shows softgel capsules coated with a formulation of 5% polysorbate 80 and 10% glycerol monostearate shortly after coating (T0). FIG. 1C shows softgel capsules coated with a formulation of 10% polysorbate 80 and 5% glycerol monostearate after one month, removed from the container. FIG. 1D shows softgel capsules coated with a formulation of 10% polysorbate 80 and 10% glycerol monostearate after 12 months.

DETAILED DESCRIPTION

Figure 2A:
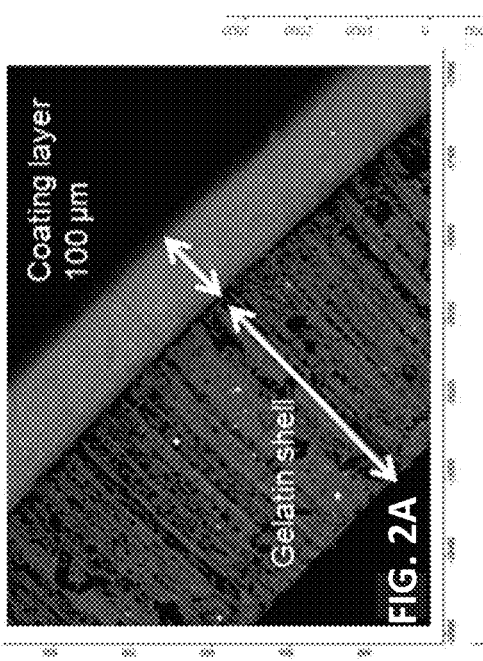
FIGS. 2A-2C show photomicrographs of the thickness of the coating film with Formulation 5 according to the Examples. The thickness of the coating is shown in FIG. 2A along the capsule body, in FIG. 2B on the sealing zone, and in FIG. 2C the cross-section of the softgel capsule, illustrating the homogeneity of the coating film in cross-section.

In one embodiment, the controlled release polymers are enteric copolymers like polymethacrylates (copolymers of methacrylic acid and either methylmethacrylate or ethyl acrylate) (EUDRAGIT®). In certain embodiments, the copolymers are present in amounts ranging from about 10% to about 30% by weight (of dry copolymer) of the enteric release composition. In certain embodiments, the copolymers are present in an amount of about 15% by weight (of dry copolymer) of the total weight of the composition.

Non-limiting examples of glidants for use in certain embodiments include mono-, di-acylglycerides such as glyceryl monostearate, and sorbitan esters such as sorbitan monopalmitate and sorbitan monolaurate. For the glidants, at least one glidant may be used, or mixtures of more than one glidant, in amounts ranging from greater than about 5% to about 15% by weight, from about 6% to about 15% by weight, and particularly about 10% by weight, based on dry copolymer content. In one embodiment of the disclosure, glycerol monostearate is the at least one glidant used.

Emulsifiers for use in certain embodiments include, but are not limited to, polyoxyethylene alkyl ethers, propylene glycol esters, glyceryl esters, sorbitan esters, polyoxyethylene castor oil derivatives, polyoxyethylene sorbitan fatty acid esters, polyoxyethylene stearates, and mixtures thereof. At least one emulsifier may be used, or mixtures of more than one emulsifier. Various embodiments include at least one emulsifier in amounts ranging from greater than about 5% to about 30% by weight, from about 6% to about 20% by weight, from about 6% to about 15% by weight, from about 6% to about 10% by weight, and more particularly about 10% by weight, based on dry copolymer content.

Non-limiting examples of polyoxethylene alkyl ethers for use in certain embodiments include polyoxyl 2 cetyl ether, polyoxyl 10 cetyl ether, polyoxyl 20 cetyl ether, polyoxyl 4 lauryl ether, polyoxyl 23 lauryl ether, polyoxyl 2 oleyl ether, polyoxyl 10 oleyl ether, polyoxyl 20 oleyl ether, polyoxyl 2 stearyl ether, polyoxyl 10 stearyl ether, polyoxyl 20 stearyl ether, polyoxyl 10 stearyl ether, polyoxyl 20 cetostearyl ether, and mixtures thereof.

Examples of propylene glycol ester for use in certain embodiments include, but are not limited to, propylene glycol dicocoate, propylene glycol distearate, propylene glycol dioctanoate, propylene glycol dipelargonate, propylene glycol diundecanoate, propylene glycol monostearate, propylene glycol monohydroxystearate, propylene glycol monolaurate, propylene glycol monomyristate, propylene glycol monooleate, and mixtures thereof.

Examples of glyceryl esters for use in certain embodiments include, but are not limited to, glyceryl monooleate, glyceryl monostearate, glyceryl palmitostearate, and mixtures thereof.

Examples of sorbitan esters for use in certain embodiments include, but are not limited to, sorbitan di-isostearate, sorbitan dioleate, sorbitan monolaurate, sorbitan monoisostearate, sorbitan monooleate, sorbitan monopalmitate, sorbitan monostearate, sorbitan sesqui-isostearate, sorbitan sesquioleate, sorbitan sesquistearate, sorbitan tri-isostearate, sorbitan trioleate, sorbitan tristearate, and mixtures thereof.

Examples of polyoxyethylene castor oil derivatives for use in certain embodiments include, but are not limited to, polyoxyl 5 castor oil, polyoxyl 9 castor oil, polyoxyl 15 castor oil, polyoxyl 35 castor oil, polyoxyl 40 castor oil, polyoxyl 40 hydrogenated castor oil, polyoxyl 60 hydrogenated castor oil, and mixtures thereof. In certain embodiments, the polyoxyethylene castor oil derivatives are polyoxyl 35 castor oil (CREMOPHOR® EL) or polyoxyl 40 hydrogenated castor oil (CREMOPHOR® RH40) or mixtures thereof.

Examples of polyoxyethylene sorbitan fatty acid esters for use in certain embodiments include, but are not limited to, polysorbate 20, polysorbate 21, polysorbate 40, polysorbate 60, polysorbate 61, polysorbate 65, polysorbate 80, polysorbate 81, polysorbate 85, polysorbate 120, and mixtures thereof.

Examples of polyoxyethylene stearates for use in certain embodiments include, but are not limited to, polyoxyl 6 stearate, polyoxyl 8 stearate, polyoxyl 12 stearate, polyoxyl 20 stearate, and mixtures thereof.

In one embodiment according to the disclosure, polysorbate 80 (Polyoxyethylene (20) sorbitan monooleate, sold, for example, as TWEEN 80®; Montanox® 80, Eumulgin® SMO, Crillet® 4) is the at least one emulsifier.

Non-limiting examples of plasticizers for use in certain embodiments include polyethylene glycol, glycerol, sorbitol, dioctyl-sodium sulfosuccinate, triethyl citrate (TEC), tributyl citrate, 1,2-propyleneglycol, mono-, di, or tri-acetates of glycerol, dibutyl sebecate, di- and triethyl phtalate, polyethylene glycol 6000, and mixtures thereof. At least one plasticizer may be used, or mixtures of more than one plasticizer, at about 10% to 25% by weight, particularly about 20% by weight. In one embodiment, triethyl citrate is the at least one plasticizer used.

Optionally, some embodiments comprise at least one additive selected from pigments, colorants, antifoam agents, antioxidants, waxes, and mixtures thereof.

Suitable pigments or colorants include pharmaceutically acceptable coloring agents, food acceptable colorants, or mixtures thereof. Examples of such colorants include, but are not limited to, azo-, quinophthalone-, triphenylmethane-, xanthene- or indigoid dyes; iron oxides or hydroxides; titanium dioxide; natural dyes; and mixtures thereof. Additional examples include patent blue V, acid brilliant green BS, red 2G, azorubine, ponceau 4R, amaranth, D+C red 33, D+C red 22, D+C red 26, D+C red 28, D+C yellow 10, yellow 2 G, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, anthocyanines, turmeric, cochineal extract, chlorophyllin, canthaxanthin, caramel, betanin and CANDURIN® pearlescent pigments. CANDURIN® is manufactured and marketed by Merck KGaA, Darmstadt, Germany and consists of titanium dioxide and/or iron oxide (approved food and pharmaceutical colorants in many countries) and potassium aluminum silicate as a color carrier.

In some embodiments, the optional colorants or mixtures thereof are present in an amount up to about 5% by weight, e.g., from about 0 to about 2.5% by weight, and from about 0 to about 1.5% by weight of the total weight of the composition.

Suitable antifoam agents include pharmaceutically acceptable antifoam agents, food acceptable antifoam agents, or mixtures thereof. Examples of such antifoam agents include, but are not limited to, silicone oils such as poly(dimethyl siloxane.

Suitable antioxidants are any compound or composition which is capable of counteracting the damaging effects of oxidation, including but not limited to enzymes and other substances, such as vitamin C, vitamin E, and beta carotene, and mixtures thereof.

Suitable waxes include, but are not limited to, pharmaceutically acceptable and/or food grade waxes, including but not limited to carnauba wax and beeswax.

In some embodiments, compositions according to the instant disclosure allow direct coating of the softgel capsules with excellent adhesion capacity without prior removal of lubricants applied on the outside of the capsule shell during the softgel manufacturing, and also without prior application of a subcoating on the softgel capsules.

In certain embodiments, the instant disclosure is also directed to a method of making an enterically-coated softgel dosage form. In certain embodiments the method comprises contacting the dosage form with an enteric coating composition. The contacting of the dosage form with the enteric coating composition according to the present disclosure may be achieved, for example, by spray coating in a fluidized bed coater or in a side-vented pan coater.

Softgel capsules for use in various embodiments of the compositions and methods of the instant disclosure include any softgel capsule of any configuration, size or shape, including but not limited to SGCAPS™ soft gelatin capsules available from CAPSUGEL®. The softgel capsules or soft gelatin containers for use in various embodiments may be any size, and include but are not limited to round, oval, oblong, tube, or elliptical shaped softgel capsules. Of particular interest are softgel capsules and softgel dosage forms with unfavorable geometries, such as oblong shaped capsules including but not limited to size 20 oblong softgel capsules. According to various embodiments of the present disclosure, the softgel capsules may be filled with any fill compatible with the softgel capsule for which enteric delivery is desired or needed.

The compositions and methods of the present disclosure are useful for, but not limited to, for example, oral administration of at least one of pharmaceuticals, veterinary products, foods, and dietary supplements to humans or animals.

EXAMPLES

Table 1 gives examples of the compositions in weight percentages of the additives in the coating compositions tested.

TABLE 1

| | Formulation 1 | Formulation 2 | Formulation 3 | Formulation 4 | Formulation 5 |
|---|---|---|---|---|---|
| Composition of additives (w/w, as % of dry copolymer) | | | | | |
| Triethylcitrate (TEC) | 20 | 20 | 20 | 20 | 20 |
| Glyceryl monostearate (GMS) | — | 5 | 5 | 10 | 10 |
| polysorbate 80 | 10 | 5 | 10 | 5 | 10 |

Preparation and application of the coating formulations: 5 or 10% (w/w, based on dry polymer content) of polysorbate 80, and 5 or 10% (w/w, based on dry polymer content) of glyceryl monostearate, were mixed at 80° C. and homogenized using magnetic stirring. Then, approximately half of the final quantity of the purified water heated to 80° C. was added.

When the solution was homogeneous, 20% (w/w, based on dry polymer content) of triethyl citrate (TEC) was added. The formulation was homogenized using homogenization equipment such as an ULTRA-TURRAX® T25 (speed around 10,000 rpm) for at least 10 min, before the addition of the remaining quantity of purified water.

The coating polymer, under the form of an aqueous dispersion of an anionic copolymer based on methacrylic acid and ethyl acrylate, i.e. EUDRAGIT® L30-D55 (Poly (methacrylic acid-co-ethyl acrylate) 1:1) (30% dry copolymer), was finally added when the formulation reached a temperature below 30° C. The coating formulation was homogenized using an appropriate mixing device such as a 3-helix blade for a minimum of 60 minutes at an appropriate speed allowing the formation of a small vortex in the solution. A low mixing speed was maintained using the 3-helix blade until the end of the coating step. The resulting coating formulation was passed through a 0.5 mm sieve.

Softgel capsules (20 oblong from CAPSUGEL®, liquid oil fill) were coated in a perforated pan coater (such as a 4M8TriX pan coater) according to the manufacturer's standard procedures, i.e., preheating of the softgel capsules in the drum, spraying the coating formulation on the softgel capsules, and drying the resulting softgel capsules. The capsule coating formulations were sprayed onto the softgel capsules under the appropriate process conditions to obtain a coating level of about 7% to 12% (w/w), measured as a weight gain in comparison with the non-coated softgel capsules.

Table 2 shows the compositions of the coating formulations tested (w/w, according to final composition weight) and gives results for the coating of softgel capsules with Formulations 1, 2, 3, 4, and 5.

TABLE 2

| | Formulation 1 | Formulation 2 | Formulation 3 | Formulation 4 | Formulation 5 |
|---|---|---|---|---|---|
| Composition of the coating formulation (w/w, according to final composition weight) | | | | | |
| Polymer (% dry content) | 15.00 | 15.00 | 15.00 | 15.00 | 15.00 |
| Triethyl citrate | 3.00 | 3.00 | 3.00 | 3.00 | 3.00 |
| Glyceryl monostearate | — | 0.75 | 0.75 | 1.50 | 1.50 |
| Polysorbate 80 | 3.00 | 0.75 | 1.50 | 0.75 | 1.50 |
| Water | 79.00 | 80.50 | 79.75 | 79.75 | 79.00 |
| Characterization at T0 | | | | | |
| Weight gain of coating (%) | 10.8 | 8.0 | 7.5 | 8.2 | 8.3 |
| Disintegration testing (n = 6) | | | | | |
| pH 1.2 | >2 h 00 min | >2 h 00 min | >2 h 00 min | >2 h 00 min | >2 h 00 min |
| pH 6.8 | ~0 h 11 min | ~0 h 08 min | ~0 h 12 min | ~0 h 14 min | ~0 h 10 min |
| Texture analyzer (n = 10) Results at 1st crack | | | | | |
| Applied force (N) | 112 | 50 | 146 | 25 | 123 |
| Displacement (mm) | >3 mm | 1.5 mm | >3 mm | 1.9 mm | >3 mm |
| | | Crack at T0 | | Crack at T0 | |
| | Stability study | No stability study | Stability study | No stability study | Stability study |
| Characterization after 1 mo. storage at 25° C./60% RH | | | | | |
| Disintegration testing (n = 3) | Not performed due to stickiness of capsules after storage | | Not performed due to stickiness of capsules after storage | | |
| pH 1.2 | | | | | >2 h 00 min |
| pH 6.8 | | | | | ~0 h 09 min |
| Texture analyzer (n = 10) Results at 1st crack | | | | | |
| Applied force (N) | | | | | 77 |
| Displacement (mm) | | | | | >3 mm |
| Characterization after 6 mo. storage at 25° C./60% RH | | | | | |
| Disintegration testing (n = 3) | | | | | |
| pH 1.2 | | | | | >2 h 00 min |
| pH 6.8 | | | | | ~0 h 11 min |
| Texture analyzer (n = 10) Results at 1st crack | | | | | |
| Applied force (N) | | | | | 64 |
| Displacement (mm) | | | | | >3 mm |

A disintegration test was used to evaluate the enteric properties of the coated capsules. The test was performed according to USP standards (USP35-NF30). Six capsules underwent the following steps in a Sotax DT2 disintegration apparatus: 2 hours of exposure to an acidic buffer (0.1 N hydrochloric acid; pH=1.2) at 37° C. followed by testing in a phosphate buffer (pH=6.8) at 37° C. until complete disintegration.

An objective of the testing was to define the suitable composition of an enteric coating formulation to be used to provide enteric properties to dosage forms with unfavorable geometries, including but not limited to, size 20 oblong softgel capsules. Therefore, the influence on the physical-mechanical properties of the coating applied to dosage forms with unfavorable geometry of two additives added to the enteric coating formulation, i.e. polysorbate 80 and glycerol monostearate, was analyzed. The two additives were formulated with Eudragit® L30-D55 with 20% of dry polymer and triethyl citrate as the plasticizer.

In addition to enteric properties, additional criteria were analyzed for discriminating the formulations including: (i) adhesion between the gelatin capsule and the coating; (ii) mechanical properties of the coated capsules following strain; (iii) stickiness of the capsules upon storage, and (iv) stability upon storage under ICH conditions (25° C./60% RH, 30° C./65% RH and 40° C./75% RH). Compositions were defined in comparison with the ratios traditionally used for additives to be used with polymeric coatings (Table 1). Results are summarized in Table 2.

Figure 2B:
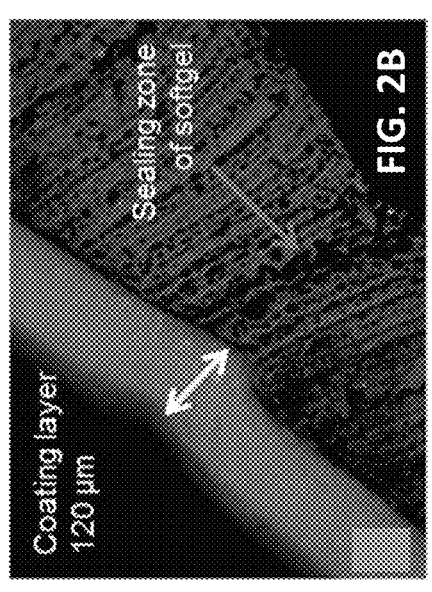
Figure 2C:
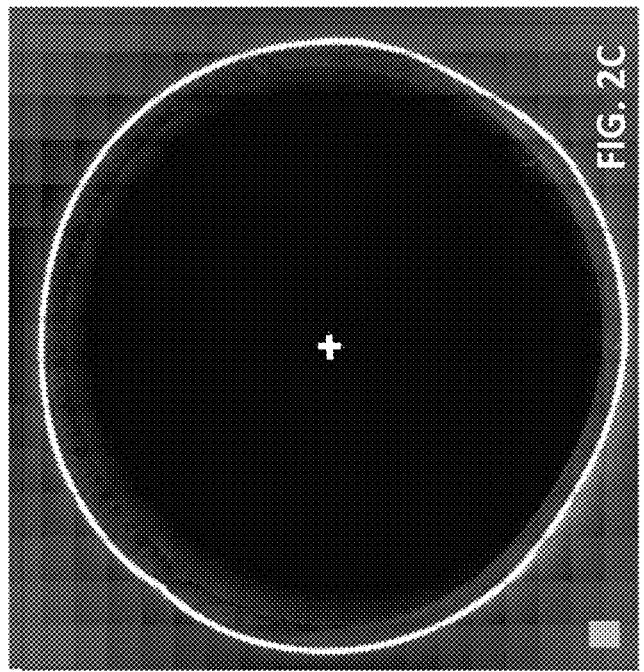

Surprisingly, it was found that polysorbate 80 of about 1.5% (of the final composition weight) of a 15% dry copolymer content composition (corresponding to greater than 5% by weight calculated according to dry copolymer weight) resulted in favorable adhesion and flexibility of the coating on the size 20 oblong softgel capsules. This content was found to prevent the coating from cracking (see FIGS. 1B and 1D). The minimum content, which can also be defined to be above about 5% calculated by weight of dry copolymer, is higher than the maximum amounts of polysorbate 80 reported in the literature (i.e., commonly 1 to 3% (w/w) of dry copolymer). (Cole et al., 2002, *Int. J. Pharm.* 231, 83-95, Wesseling et al., 1999, *Eur. J Pharm. Biopharm.* 47, 73-78)]. Moreover, GMS, acting as an anti-tacking agent, only proved its efficiency on enteric coated size 20 oblong softgel capsules when a percentage above about 5% by weight of dry polymer was added. Otherwise severe stickiness of the capsules was observed during storage, a phenomenon more pronounced when placed under stressful storage conditions (40° C./75% RH). These surprisingly high quantities of polysorbate 80 and GMS are particularly suitable for coating unfavorable capsule geometries such as size 20 oblong softgel capsules which could deform more strongly due to the fact that these capsules have a high length/width ratio and present also a larger contact surface which could lead to increased stickiness. Furthermore, the enteric coating composition defined above and based on Eudragit® L30-D55, 20% TEC, 10% polysorbate 80 and 10% GMS (expressed as a weight percentage of dry copolymer) also showed a good film homogeneity along the capsule body (FIG. 2c), successfully covering the sealing zone with a thickness of around 100 μm to 120 μm for a weight gain of 8.3% (around 13 mg/cm$^2$) (FIGS. 2a and 2b.)

Exemplary ranges suitable for the formulation compositions are:
Enteric Polymer in amounts ranging from about 10% to about 30% (w/w of the final composition); Triethyl citrate (TEC) in amounts ranging from about 10% to about 25% (w/w, based on dry polymer content); Glyceryl monostearate (GMS) ranging from greater than about 5% to about 15%, or about 6% to about 12%, or about 6% to about 10% (w/w, based on dry polymer content); polysorbate 80 ranging from greater than about 5% to about 30%, or from about 6% to about 20%, or from about 6% to about 10% (w/w, based on dry polymer content).

Another embodiment comprises an enteric coating composition, comprising: at least one methacrylic acid/acrylate copolymer present in an amount of about 15% by dry copolymer weight of the composition; at least one glidant is present in an amount of about 1.5% by weight of the composition; at least one emulsifier is present in an amount of about 1.5% by weight of the composition; and at least one plasticizer is present in an amount of about 3% by weight of the composition. In one embodiment, the enteric coating composition comprises wherein the at least one glidant is glycerol monostearate; the at least one emulsifier is polysorbate 80; and the at least one plasticizer is triethyl citrate (TEC).

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What we claim is:
1. A softgel dosage form enteric coating composition comprising:
an aqueous coating composition consisting of:
a methacrylic acid/acrylate copolymer, in an amount ranging from about 10% to about 30% of dry copolymer by weight of the aqueous coating composition;
at least one glidant, in an amount ranging from greater than 5% to about 15% by weight of the dry copolymer;
at least one emulsifier, in an amount ranging from greater than about 5% to about 30% by weight of the dry copolymer;
at least one plasticizer, selected from the group consisting of polyethylene glycol, glycerol, sorbitol, dicotyl-sodium sulfosuccinate, triethyl citrate (TEC), tributyl citrate, mono-, di, or tri-acetates of glycerol, dibutyl sebecate, di- and triethyl phthalate, polyethylene glycol 6000, and mixtures thereof, in an amount ranging from about 10% to about 25% by weight of the dry copolymer; and
water.

2. The enteric coating composition according to claim 1, wherein:
the at least one glidant is present in an amount of from about 10% to about 15% by weight of the dry copolymer; and
the at least one emulsifier is present in an amount of from about 10% to about 30% by weight of the dry copolymer.

3. The enteric coating composition according to claim 2, wherein the at least one glidant is glycerol monostearate, the at least one emulsifier is polysorbate 80, and the at least one plasticizer is triethyl citrate (TEC).

4. The enteric coating composition according to claim 1, wherein the methacrylic acid/acrylate copolymer comprises copolymer(methacrylic acid/ethyl acrylate), copoly(methacrylic acid/methyl methacrylate), a combination of methacrylic acid, methyl methacrylate, ethyl acrylate, or a mixture thereof.

5. A softgel dosage form enteric coating composition consisting of:
poly(methacrylic acid-co-ethyl acrylate) 1:1 (EUDRAGIT® L30-D55) copolymer, in an amount ranging from about 10% to about 30% by weight of the composition;
glyceryl monostearate in an amount ranging from greater than 5% to about 15% by weight based on dry copolymer weight;
polysorbate 80 in an amount ranging from greater than 5% to about 30% by weight based on dry copolymer weight;
triethyl citrate in an amount ranging from about 10% to about 25% by weight based on dry copolymer weight;
an additive selected from the group consisting of pigments, colorants, antifoam agents, antioxidants, waxes, or any mixture thereof; and
water.

6. A softgel dosage form enteric aqueous coating composition consisting of:
methacrylic acid/acrylate copolymer present in an amount of about 15% of dry copolymer by weight of the aqueous composition;
glidant present in an amount of about 1.5% by weight of the composition;
emulsifier present in an amount of about 1.5% by weight of the composition;
plasticizer present in an amount of about 3% by weight of the composition;
an additive selected from the group consisting of pigments, colorants, antifoam agents, antioxidants, waxes, or any mixture thereof; and
water.

7. The enteric coating composition according to claim 6, wherein the glidant is glycerol monostearate; the emulsifier is polysorbate 80; and the plasticizer is triethyl citrate (TEC).

8. The softgel dosage form enteric coating composition according to claim 1, wherein the at least one glidant is present in an amount of about 10% weight of the dry copolymer.

9. The softgel dosage form enteric coating composition according to claim 1, wherein the at least one emulsifier is present in an amount of about 10% by weight of the dry copolymer.

10. The softgel dosage form enteric coating composition according to claim 8, wherein the at least one emulsifier is present in an amount of about 10% by weight of the dry copolymer.

11. The softgel dosage form enteric coating composition according to claim 1, wherein the methacrylic acid/acrylate copolymer is present in an amount of about 15% by weight of the dry copolymer by weight of the aqueous coating composition.

12. A softgel dosage form enteric coating composition comprising:

an aqueous coating composition consisting of:
a methacrylic acid/acrylate copolymer, in an amount ranging from about 10% to about 30% of dry copolymer by weight of the aqueous coating composition;
a glidant, in an amount ranging from greater than 5% to about 15% by weight of the dry copolymer;
an emulsifier, in an amount ranging from greater than about 5% to about 30% by weight of the dry copolymer;
a plasticizer, selected from the group consisting of polyethylene glycol, glycerol, sorbitol, dicotyl-sodium sulfosuccinate, triethyl citrate (TEC), tributyl citrate, mono-, di, or tri-acetates of glycerol, dibutyl sebecate, di- and triethyl phthalate, polyethylene glycol 6000, and mixtures thereof, in an amount ranging from about 10% to about 25% by weight of the dry copolymer;
an additive selected from the group consisting of pigments, colorants, antifoam agents, antioxidants, waxes, or any mixture thereof; and
water.

* * * * *